(12) United States Patent
Belanoff

(10) Patent No.: US 7,402,578 B2
(45) Date of Patent: Jul. 22, 2008

(54) METHODS FOR INHIBITING COGNITIVE DETERIORATION IN ADULTS WITH DOWN'S SYNDROME

(75) Inventor: Joseph K. Belanoff, Woodside, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 474 days.

(21) Appl. No.: 10/230,575

(22) Filed: Aug. 28, 2002

(65) Prior Publication Data

US 2003/0064974 A1 Apr. 3, 2003

Related U.S. Application Data

(60) Provisional application No. 60/316,653, filed on Aug. 31, 2001.

(51) Int. Cl.
*A61K 31/56* (2006.01)

(52) U.S. Cl. .................. 514/179; 514/178; 424/145.1

(58) Field of Classification Search ............... 514/178, 514/167, 169, 177, 179
See application file for complete search history.

(56) References Cited

U.S. PATENT DOCUMENTS 6,150,349 A 11/2000 Schatzberg et al.

FOREIGN PATENT DOCUMENTS

| WO | WO 99/17779 A1 | 4/1999 |
|---|---|---|
| WO | WO 9959596 | * 11/1999 |
| WO | WO 01/37840 A1 | 5/2001 |

OTHER PUBLICATIONS

Sekijima et al. European Neurology, (1998) 39 (4) 234-7.*
Beers, M., The Merck Manual of Diagnosis and Therapy (17th Ed) (1999), p. 2233-2235.*
Aylward, Elizabeth H. et al.; "MRI Volumes fo the Hippocampus and Amygdala in Adults with Down's Syndrome With and Without Dementia"; *Am. J. Psychiatry*; Apr. 1999; pp. 564-568; vol. 156, No. 4.
Burt, Diana B. et al.; "Dementia in Adults With Down Syndrome: Diagnostic Challenges"; *American Journal on Mental Retardation*; 1998; pp. 130-145; vol. 103, No. 2; American Association on Mental Retardation.
Geldmacher, Davis S. et al.; "Treatment of Functional Decline in Adults with Down Syndrome Using Selective Serotonin-Reuptake Inhibitor Drugs"; *J. Geriatr. Psychiatry Neurol.*; 1997; pp. 99-104; vol. 10.
Iannello, R. C. et al.; "Oxidative stress and neural dysfunction in Down Syndrome"; *J. Neural Transm.*; 1999; pp. 257-267; vol. 57 [Suppl]; Springer-Verlag.
Johannsen, Peter et al.; "The Prevalence of Dementia in Down Syndrome"; *Dementia*; 1996; pp. 221-225; vol. 7; S. Karger AG; Basel.
Kesslak, J. P. et al.; "Magnetic resonance imaging analysis of age-related changes in the brains of individuals with Down's Syndrome"; *Neurology*; Jun. 1994; pp. 1039-1045; vol. 44.
Murdoch, J. C. et al.; "Hypothalamic-pituitary-adrenocortical function in adults with Down's Syndrome"; *J. Ment. Defic. Res.*; 1979; pp. 157-162; vol. 23.
EMBASE Database on ACS; Accession No. 1999057454; Oitzl, M. S. et al.; "Continuous blockade of brain glucocorticoid receptors facilitates spatial learning and memory in rats"; *European Journal of Neuroscience*; 1998; pp. 3759-3766; vol. 10, No. 12; Abstract.
Tuor, U.I. and M.R. Del Bigio; "Protection against hypoxic-ischemic damage with corticosterone and dexamethasone; inhibition of effect by a glucocorticoid antagonist, RU38486"; *Brain Research*; 1996; pp. 258-262; vol. 743; Elsevier Science B.V.

* cited by examiner

*Primary Examiner*—Sreeni Padmanabhan
*Assistant Examiner*—L Williams
(74) *Attorney, Agent, or Firm*—Townsend and Townsend and Crew LLP

(57) ABSTRACT

This invention generally pertains to the field of psychiatry. In particular, this invention pertains to the discovery that agents capable of inhibiting the binding of cortisol to its receptors can be used in methods for preventing or reversing cognitive deterioration in adults with Down's syndrome. Mifepristone, a potent specific glucocorticoid receptor antagonist, can be used in these methods. The invention also provides a kit for preventing or reversing cognitive deterioration in a DS patient including a glucocorticoid receptor antagonist and instructional material teaching the indications, dosage and schedule of administration of the glucocorticoid receptor antagonist.

15 Claims, No Drawings

METHODS FOR INHIBITING COGNITIVE DETERIORATION IN ADULTS WITH DOWN'S SYNDROME

CROSS REFERENCE TO RELATED APPLICATIONS

The present application claims priority to U.S. Ser. No. 60/316,653 filed Aug. 31, 2001 herein incorporated by reference in its entirety.

FIELD OF THE INVENTION

This invention relates to the discovery that agents capable of inhibiting the biological action of the glucocorticoid receptor can be used in methods for preventing, reversing, or inhibiting cognitive deterioration in adults with Down's syndrome.

BACKGROUND OF THE INVENTION

Down's syndrome (DS) is the most common genetic cause of mental retardation and probably the earliest identified condition associated with mental retardation (Pulsifer, *J Int Neuropsychol Soc* 2:159-76 (1996). DS arises from one of three chromosomal abnormalities. Most commonly (95% of cases) DS is the result of trisomy 21, or the presence of an extra chromosome 21 in otherwise diploid cells. Trisomy 21 usually results from nondisjunction of chromosome 21 during meiosis of the gametes, and brings the total number of chromosomes in the adult offspring to 47. DS may also result (in about 2-4% of cases) from translocation events, occurring when a fragment of chromosome 21 becomes attached to another chromosome, most typically chromosome 14. The rarest form of DS(about 1-4% of cases) results from nondisjunction of chromosome 21 during early embryogenesis. Such individuals are mosaic, with both normal and trisomic cells being present.

DS individuals are almost invariably cognitively impaired, with most having an IQ between 40 and 60, although IQ scores within the normal range are possible (Epstein, in Scriver et al. eds., *The metabolic basis of inherited diseases*, New York: McGraw-Hill (1989)). Generally, significant developmental delays are apparent in DS child in infancy and early childhood (see Pulsifer, supra).

Superimposed on this early cognitive impairment, however, is a more serious deterioration of cognition that begins to appear as individuals with DS age. Adults with DS are at high risk for developing clinical dementia similar to that observed in Alzheimer's disease. Clinical dementia is seen in 25-30% of DS individuals by age 40, and in 75% of DS individuals at age 60 (Lai & Williams, *Arch Neuro* 46:849-53 (1989); Johanson et al., *Dementia* 2:159-168 (1991)). Other individuals display marked cognitive deterioration but do not meet the diagnostic criteria for clinical dementia. (Johannsen et al., *Dementia* 7:221-5 (1996); Burt et al., *Am J Ment Retard* 103:140-45 (1998)). Reported manifestations of cognitive deterioration in adults with DS include memory loss, anomia, apraxia, and decline in self-help skills (Lott & Lai, *Annals Neurology* 12:210-215 (1982); Young & Kramer, *Mental Retard* 29:75-9 (1991); Haxby & Shapiro, in Nadel & Epstein eds., *Alzheimer's disease and Down syndrome*, New York: Wiley-Liss (1992)). With modern medical treatment, over half of individuals with DS will survive into their fifties, and 13.5% will still be alive at age 68 (Baird & Sadovnick, *Hum Genet* 82:291-2 (1989)). Accordingly, the problem of cognitive deterioration in adults with DS is severe and growing.

No effective treatment for the cognitive impairment and decline of DS individuals is known. While multiple attempts to treat cognitive deterioration in DS individuals have been reported, none has achieved significant success. Geldmacher et al. (*J Geriatr Psychiatry Neurol* 10:99-104 (1997)) treated DS adults with selective serotonin-reuptake inhibitors (SSRIs), but reported improvement only of non-cognitive behavioral symptoms. Based on the theory that the cognitive deficits observed in DS may be linked to dysfunction of the cholinergic system, encouraging results in small-scale trials of donepezil (Kishani et al., *Lancet* 353:1064 (1999)) and nicotine (Seidl et al., *Lancet* 356:1409-10 (2000)) have been reported. However, randomized clinical trials have yet to validate these studies, and both nicotine and donepezil have drawbacks as therapeutic agents. Piracetam, a drug acting on glutamatergic neurotransmission and reported to enhance cognitive function, has been evaluated in DS children but failed to enhance cognitive function (Lobaugh et al., *Arch Pediatr Adolesc Med* 155:442-8 (2001)). Thus, there is a need for an effective therapy to prevent, inhibit, or reverse the cognitive deterioration seen in DS adults.

Cortisol, a glucocorticoid hormone which is secreted in response to ACTH (corticotropin), shows circadian rhythm variation, and further, is an important element in responsiveness to many physical and psychological stresses. It has been proposed that, with age, the cortisol regulatory system becomes hyperactivated in some individuals, resulting in hypercortisolemia. It has additionally been postulated that high levels of cortisol are neurotoxic, particularly in the hippocampus, a brain structure that is thought to be central to the processing and temporary storage of complex information and memory (see, e.g., Sapolsky et al., Ann. NY Acad. Sci. 746:294-304, 1994; Silva, Annu. Rev. Genet. 31:527-546, 1997; de Leon et al., J. Clin. Endocrinol & Metab. 82:3251, 1997; Maeda et al., supra).

Studies of human subjects who have received treatment with exogenous glucocorticoids at therapeutic levels have suggested that glucocorticoids may play a role in short-term, reversible memory impairment. (see, e.g., Wolkowitz et al., Am J. Psychiatry 147:1297-1303, 1990; Keenan et al., Neurology 47:1396-1402, 1996; Newcomer et al., Arch Gen. Psychiatry 56:527-533, 1999). Furthermore, it has been suggested that basal levels of cortisol that are chronically at the high end of the normal range, i.e., levels that correspond to peak circadian values or approximate those levels seen during stress, contribute to the impaired cognitive performance and loss of hippocampal-mediated memory function observed in aging (see, e.g., Lupien et al., J. Neurosci. 14:2893-2903, 1994; Lupien et al., Nat. Neurosci 1:69-73, 1998).

Basal cortisol levels are similar in DS and non-DS individuals (Murdoch et al., J Ment Defic Res 23:157-62 (1979); Ramunni et al., J Endocrinol Invest 22S10:5708 (1999)). Impaired activity of the HPA axis in response to ACTH has been reported in DS individuals (Murdoch et al., supra) but the significance of this finding is unknown. Hence, there has been no evidence prior to this invention that a glucocorticoid receptor antagonist can be an effective agent to prevent or reverse cognitive deterioration in adults with DS, especially in patients having cortisol levels that fall within a normal range. Many of the actions of cortisol are mediated by binding to the type I (mineralocorticoid) receptor, which is preferentially occupied, relative to the type II (glucocorticoid) receptor, at physiological cortisol levels. As cortisol levels increase, more glucocorticoid receptors are occupied and activated. Because cortisol plays an essential role in metabolism, inhibition of all cortisol-mediated activities, however, would be fatal. Therefore, antagonists that specifically prevent type II glucocorticoid receptor functions, but do not antagonize type I mineralocorticoid receptor functions are of particular use in this invention. RU486 and similar antagonists are examples of this category of receptor antagonists.

The present inventors have determined that glucocorticoid receptor antagonists such as RU486 are effective agents for preventing or reversing cognitive deterioration in DS adults with normal, increased, or decreased cortisol levels. The present invention therefore fulfills the need for an effective preventive measure for cognitive deterioration in DS patients by providing methods of administering glucocorticoid receptor antagonists to improve cognitive function in DS patients.

SUMMARY OF THE INVENTION

The invention provides a method of inhibiting or reversing cognitive deterioration in an adult with Down's syndrome. The method comprises administration of a therapeutically effective amount of a glucocorticoid receptor antagonist to the patient, with the proviso that the patient be not otherwise in need of treatment of with a glucocorticoid receptor antagonist.

In another embodiment of the invention, the glucocorticoid receptor antagonist comprises a steroidal skeleton with at least one phenyl-containing moiety in the 11-beta position of the steroidal skeleton. The phenyl-containing moiety in the 11-beta position of the steroidal skeleton can be a dimethylaminophenyl moiety. In alternative embodiments, the glucocorticoid receptor antagonist comprises mifepristone, or, the glucocorticoid receptor antagonist is selected from the group consisting of RU009 and RU044.

In other embodiments, the glucocorticoid receptor antagonist is 4a(S)-Benzyl-2(R)-prop-1-ynyl-1,2,3,4,4a,9,10,10a (R)-octahydro-phenanthrene-2,7-diol, 4a(S)-Benzyl-2(R)-chloroethynyl-1,2,3,4,4a,9,10,10a(R)-octahydro-phenanthrene-2,7-diol, or (11b, 17b)-11-(1,3-benzodioxol-5-yl)-17-hydroxy-17-(1-propynyl)estra-4,9-dien-3-one.

In other embodiments, the glucocorticoid receptor antagonist is administered in a daily amount of between about 0.5 to about 20 mg per kilogram of body weight per day; between about 1 to about 10 mg per kilogram of body weight per day; or between about 1 to about 4 mg per kilogram of body weight per day. The administration can be once per day. In alternative embodiments, the mode of glucocorticoid receptor antagonist administration is oral, or by a transdermal application, by a nebulized suspension, or by an aerosol spray.

The invention also provides a kit for inhibiting or reversing cognitive deterioration in a human with DS, the kit comprising a glucocorticoid receptor antagonist; and, an instructional material teaching the indications, dosage and schedule of administration of the glucocorticoid receptor antagonist. In alternative embodiments, the instructional material indicates that the glucocorticoid receptor antagonist can be administered in a daily amount of about 0.5 to about 20 mg per kilogram of body weight per day, of about 1 to about 10 mg per kilogram of body weight per day, or about 1 to about 4 mg per kilogram of body weight per day. The instructional material can indicate that cortisol contributes to cognitive deterioration in DS patients, and that the glucocorticoid receptor antagonist can be used to prevent or reverse such deterioration. In one embodiment, the glucocorticoid receptor antagonist in the kit is mifepristone. The mifepristone can in tablet form.

A further understanding of the nature and advantages of the present invention is realized by reference to the remaining portions of the specification and claims.

All publications, patents and patent applications cited herein are hereby expressly incorporated by reference for all purposes.

DEFINITIONS

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being; or, in some situations, preventing the onset of dementia. The treatment or amelioration of symptoms can be based on objective or subjective parameters; including the results of a physical examination, neuropsychiatric exams, and/or a psychiatric evaluation. For example, the methods of the invention successfully treat cognitive deterioration in a DS patient by improving performance of memory task tests and/or slowing or preventing the rate of, or extent of, cognitive decline.

The term "Down's syndrome" refers to a condition caused by partial or complete aneuploidy of human chromosome 21, or dysregulation of chromosome 21 gene expression. Trisomy, translocation, or mosaicism of chromosome 21 give rise to Down's syndrome.

The term "adult" refers to a person aged 18 years or greater.

The term "cognitive deterioration" refers to a loss of ability to remember concrete facts (names or objects) or to solve logical problems.

The term "dementia" refers to a psychiatric condition in its broadest sense, as defined in American Psychiatric Association: Diagnostic and Statistical Manual of Mental Disorders, Fourth Edition, Washington, D.C., 1994 ("DSM-IV"). The DSM-IV defines "dementia" as characterized by multiple cognitive deficits that include impairments in memory and lists various dementias according to presumed etiology. The DSM-IV sets forth a generally accepted standard for such diagnosing, categorizing and treating of dementia and associated psychiatric disorders.

The term "cortisol" refers to a family of compositions also referred to as hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "mifepristone" refers to a family of compositions also referred to as RU486, or RU38.486, or 17-beta-hydroxy-11-beta-(4-dimethylaminophenyl)-17-alpha-(1-propynyl)-estra-4,9-dien-3-one), or 11-beta-(4dimethylaminophenyl)-17-beta-hydroxy-17-alpha-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary; for example, RU486 has also been termed: 11B-[p-(Dimethylamino)phenyl]-
17B-hydroxy-17-(1-propynyl)-estra-4,9-dien-3-one; 11B-(4-dimethyl-aminophenyl)-17B-hydroxy-17A-(prop-1-ynyl)-estra-4,9-dien-3-one; 17B-hydroxy-11B-(4-dimethylaminophenyl-1)-17A-(propynyl-1)-estra-4,9-diene-3-one; 17B-hydroxy-11B-(4-dimethylaminophenyl-1)-17A-(propynyl-1)-E; (11B, 17B)-11-[4-dimethylamino)-phenyl]-17- hydroxy-17-(1-propynyl)estra-4,9-dien-3-one; and 11B-[4-(N,N-dimethylamino) phenyl]-17A-(prop-1-ynyl)-D-4,9-estradiene-17B-ol-3-one.

The term "specific glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" also refers to any composition or compound which inhibits any biological response associated with the binding of a GR to an agonist. By "specific", we intend the drug to preferentially bind to the GR rather than the mineralocorticoid receptor (MR) with an affinity at least 100-fold, and frequently 1000-fold.

A patient "not otherwise in need of treatment with a glucocorticoid receptor antagonist" is a patient who is not suffering from a condition which is known in the art to be effectively treatable with glucocorticoid receptor antagonists. Conditions known in the art to be effectively treatable with glucocorticoid receptor antagonists include Cushing's disease, drug withdrawal, psychosis, dementia, stress disorders, and psychotic major depression.

DETAILED DESCRIPTION OF THE INVENTION

This invention pertains to the surprising discovery that agents capable of inhibiting glucocorticoid-induced biological responses are effective for treating cognitive deterioration in individuals with Down's syndrome. The target patient is one who either has not begun age-related cognitive deterioration or has only begun to deteriorate from a baseline set as a young adult. In treating cognitive deterioration, the methods of the invention can preferably forestall the impairment of memory, and/or, the rate of, or extent of, any further decline in memory function. In one embodiment, the methods of the invention use agents that act as GR antagonists, blocking the interaction of cortisol with GR, to treat or ameliorate cognitive deterioration. The methods of the invention are effective in improving memory performance, or preventing or slowing further memory impairment or cognitive function, in a DS individual patient afflicted with either normal or increased levels of cortisol or other glucocorticoids, natural or synthetic.

Cortisol acts by binding to an intracellular, glucocorticoid receptor (GR). In humans, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same signal transduction pathways.

The biological effects of cortisol, including pathologies or dysfunctions caused by hypercortisolemia, can be modulated and controlled at the GR level using receptor antagonists. Several different classes of agents are able to act as GR antagonists, i.e., to block the physiologic effects of GR-agonist binding (the natural agonist is cortisol). These antagonists include compositions, which, by binding to GR, block the ability of an agonist to effectively bind to and/or activate the GR. One family of known GR antagonists, mifepristone and related compounds, are effective and potent anti-glucocorticoid agents in humans (Bertagna, *J. Clin. Endocrinol. Metab.* 59:25, 1984). Mifepristone binds to the GR with high affinity, with a K of dissociation $<10^{-9}$ M (Cadepond, *Annu. Rev. Med.* 48:129, 1997). Thus, in one embodiment of the invention, mifepristone and related compounds are used to prevent cognitive deterioration in adults with DS.

As the methods of the invention include use of any means to inhibit the biological effects of an agonist-bound GR, illustrative compounds and compositions which can be used to treat cognitive deterioration in DS patients are also set forth. Routine procedures that can be used to identify further compounds and compositions able to block the biological response caused by a GR-agonist interaction for use in practicing the methods of the invention are also described. As the invention provides for administering these compounds and compositions as pharmaceuticals, routine means to determine GR antagonist drug regimens and formulations to practice the methods of the invention are set forth below.

1. Diagnosis of Cognitive Deterioration in Adults with Down's Syndrome a. Identifying Down's Syndrome Patients Down's syndrome patients are usually diagnosed at birth, due to the characteristic physical features associated with trisomy 21. The physical phenotype of DS includes microcephaly, upward slanting eyes, broad neck, and hands that are small with in-curving fifth finger and a solitary simian crease across the palm. DS individuals are significantly shorter than the non-DS population, with an average height for adult males of around 5 feet and around 4.5 feet for females.

Neuropsychologically, individuals with DS display disproportionately impaired speech and expressive language skills, especially in articulation, phonology, and expressive syntax (Fowler, in Cicchetti & Beeghly eds., Children with Down Syndrome: A developmental perspective (pp. 302-328) New York: Cambridge University Press, 1990) and deficits in verbal short-term memory (Marcell & Armstrong, Am J Mental Deficiency 87:86-95 (1982); Varnhagen et al., Am J Mental Deficiency 91:398-405 (1987)). Imaging of DS patients shows they typically have reduced brain size (about 76% of normal) and reduced complexity of the convolutional pattern (Coyle et al., Brain Res Bull 16:773-87 (1986); Wisniewski, Am J Med Genet 7:274-81 (1990)). Small frontal lobes, a small operculum, a narrow superior temporal gyrus, and reduced volume of the hippocampus, cerebellum, and brainstem are typical.

Although the hallmarks of DS are evident at birth, significant declines in cognition and adaptive behavior are no more common in DS patients under 50 years of age than in adults with other forms of mental retardation. In contrast, individuals with DS over the age of 50 are much more likely to display marked cognitive deterioration (Zigman et al., Am J Ment Retard 100:403-12 (1996)). Thus, in one embodiment of the invention, antiglucocorticoid therapy is provided to a DS patient commencing at approximately 50 years of age, to forestall the onset of cognitive deterioration. However, since the neuropathological mechanisms of cognitive deterioration may commence before symptoms of cognitive deterioration become evident, GR antagonist therapy may be initiated at a younger age, e.g., at approximately 45, 40, 35, or 30 years of age. The time course of precocious aging observed in DS patients (i.e., changes in hair, skin elasticity, motor skills, and skeletal structure; see Oliver & Holland, Psychological Medicine 16:307-12 (1986)) may be used to judge when GR antagonist therapy should be initiated for a particular individual with DS.

There are various means to diagnose the onset of cognitive deterioration in a DS patient and to assess the efficacy of treatment using the methods of the invention. These include the administration of psychiatric tests to determine the CDR, the administration of memory tests, and the administration of psychiatric tests for dementia. The results of these tests may be considered in conjunction with other objective tests as described below. These means are also useful for assessing the efficacy of the methods of the invention in improving memory or decreasing or diminishing further impairment in memory or cognitive decline in a patient with DS. While the practitioner can use any set of prescribed or empirical criteria that are defined in the scientific and patent literature to diagnose the presence of DS as an indication to practice the methods of the invention, some illustrative diagnostic guidelines and examples of relevant symptoms and conditions are described below. Subjective and objective criteria can be used to measure and assess the success of a particular GR antagonist, pharmaceutical formulation, dosage, treatment schedule or regimen.

b. Assessing and Diagnosing Cognitive Deterioration and Function by Test Evidence Adults with DS, if untreated, frequently develop cognitive deterioration that may or may not progress to clinical dementia. Accordingly, cognitive deterioration in adults with DS may be measured by tests that assess cognitive impairment. Cognitive impairment can be diagnosed by formal psychiatric assessment using subjective diagnosis or objective test criteria to determine whether an individual is afflicted with cognitive impairment. The methods of the invention are preferably practiced early in the course of (in the early stages of) DS-related cognitive deterioration, and most preferably, before adult cognitive deterioration sets in. This is especially critical in the case of DS patients who may be at elevated risk for progression to Alzheimer's disease, for example, patients who bear the apolipoprotein ∈4 genotype (see, e.g., Tierney et al., Neurology 45:149-154, 1996).

Cognitive functioning can be diagnosed and evaluated using any of the many objective tests or criteria well-known and accepted in the fields of psychology or psychiatry. Objective tests can used to determine whether an individual is suffering from impaired memory function or dementia and to measure and assess the success of a particular GR antagonist, pharmaceutical formulation, dosage, treatment schedule or regimen. For example, measuring changes in cognitive ability and memory aids in the diagnosis and treatment assessment of a DS patient suffering from or at risk for cognitive deterioration. Any test known in the art can be used.

The Vineland Adaptive Behavior Scales (VABS) are a set of tests that measure cognitive function and social adaptation (Sparrow et al, Vineland Adaptive Behavior Scales—Interview Edition (Psychological Measure). Circle Pines, Minn.: American Guidance Service, 1984). Patients are rated on three subscales (communication, daily living skills, and socialization) and also receive an adaptive behavior composite score. Although individuals with show significant strength in daily living and socialization skills relative to communication skills on the VABS (Dykens et al., Am J Ment Retard 98:580-7 (1994)), scores on the VABS are often used to assess the therapeutic effects of possible treatments for DS (see, e.g., Kishani et al., Lancet 353:1064 (1999)). Decreases in any of the VABS standard scores may be indicia of DS-related cognitive deterioration; conversely, improvement in any of the VABS subscales or the adaptive behavior composite score are indicia of improvement in cognitive or adaptive function.

One measure of cognitive deterioration in DS patients is the Clinical Dementia Rating (CDR; see Hughes et al., Brit. J. Psychiat. 140:566-572, 1982 and Morris, Neurology 43:2412-2414, 1993). In determining the CDR, a patient is typically assessed and rated in each of six cognitive and behavioral categories: memory, orientation, judgment and problem solving, community affairs, home and hobbies, and personal care. The assessment may include historical information provided by the patient, or preferably, a corroborator who knows the patient well. The patient is assessed and rated in each of these areas and the overall rating, (0, 0.5, 1.0, 2.0 or 3.0) determined. A rating of 0 is considered normal. A rating of 1.0 is considered to correspond to mild dementia. A patient with a CDR of 0.5 is characterized by mild consistent forgetfulness, partial recollection of events and "benign" forgetfulness. The patient is fully oriented and exhibits little impairment in determining similarities and differences and other problem solving skills, or impairment in function in terms of the community, home, or personal care.

Another hallmark of cognitive deterioration is impaired performance on a memory task test. Memory may be measured by such tests known in the art as the Wechsler Memory Scale or a pair-associated memory task. A patient is considered to exhibit impaired performance on such a test if the score is below the education and age-adjusted cutoff for that test. Cognitive deterioration is typically characterized by impairment in delayed recall memory functions, which can be specifically addressed as a component of a memory task test. For example, impaired memory function may be documented by scoring at or below the education cutoff on the Logical Memory II subscale (Delayed Paragraph Recall) from the Wechsler Memory Scale-Revised, of which the maximum score is 25. Age and education-adjusted cutoffs are determined using methods known in the art (see, e.g., Ivnik et al. Clinc. Neuropsychol 6 (Suppl): 1-30 and 49-82, 1992; Ivnik et al. J. Consult Clin. Psychol 3: 1991; Ivnik et al., Clin. Neuropsychol. 10:262-276, 1996) An example of these cutoffs are: a) less than or equal to 8 for 16 or more years of education; b) less than or equal to 4 for 8-15 years of education and c) less than or equal to 2 for 0-7 year of education. A cutoff value may be determined, for example, by selecting a value that is 1, preferably 1.5, or more standard deviations from the norm for that education and age cohort.

"Improvement" in memory is present within the context of the present invention if there is a statistically significant difference in the direction of normality between the performance of patients treated using the methods of the invention as compared to members of a placebo group or between subsequent tests given to the same patient.

Where cognitive deterioration in adults with DS is severe, patients may meet the criteria for clinical dementia, as set forth in the DSM-IV-TR. One benefit of the present invention is prevention of dementia in DS patients. Down syndrome patients with dementia are outside the scope of this invention because dementia was previously known to be treated by glucocorticoid antagonists. One objective test for dementia is the so-called Mini-Mental State Examination (MMSE), as described by Folstein "'Mini-mental state.' A practical method for grading the cognitive state of patients for the clinician." J. Psychiatr. Res. 12:189-198, 1975. The MMSE evaluates the presence of global intellectual deterioration. See also Folstein "Differential diagnosis of dementia. The clinical process." Psychiatr Clin North Am. 20:45-57, 1997. The MMSE is a long-recognized means to evaluate the onset of dementia and the presence of global intellectual deterioration, as seen in Alzheimer's disease and multi-infarct dementia. See, e.g., Kaufer, J. Neuropsychiatry Clin. Neurosci. 10:55-63, 1998; Becke, Alzheimer Dis Assoc Disord. 12:54-57, 1998; Ellis, Arch. Neurol. 55:360-365, 1998; Magni, Int. Psychogeriatr. 8:127-134, 1996; Monsch, Acta Neurol. Scand. 92:145-150, 1995. The MMSE is scored from 1 to 30. The MMSE does not evaluate basic cognitive potential, as, for example, the so-called IQ test. Instead, it tests intellectual skills. A person of "normal" intellectual capabilities will score a "30" on the MMSE objective test (however, a person with a MMSE score of 30 could also score well below "normal" on an IQ test). Accordingly, the methods of the invention are appropriately administered when an individual scores 30 on the MMSE. Because it is possible for a "normal" individual to score less than 30 upon a single administration of a test, a "normal" indication on the test is considered to be a score of 30 on at least one test in three administrations of the test.

Another means to evaluate dementia is the Alzheimer's Disease Assessment Scale (ADAS-Cog), or a variation termed the Standardized Alzheimer's Disease Assessment Scale (SADAS). It is commonly used as an efficacy measure in clinical drug trials of Alzheimer's disease and related disorders characterized by cognitive decline. SADAS and ADAS-Cog were not designed to diagnose Alzheimer's disease; they are useful in characterizing symptoms of dementia and are a relatively sensitive indicator of dementia progression. (See, e.g., Doraiswamy, Neurology 48:1511-1517, 1997; and Standish, J. Am. Geriatr. Soc. 44:712-716, 1996.)

The evaluation for the presence of cognitive deterioration can also utilize a combination of subjective diagnosis and objective testing. For example, family history and history provided by the patient as well as other individuals can be used as a component in the determination of cognitive deterioration. Other tests may also be considered in diagnosing cognitive deterioration. In one study (Petersen et al., Arch Neurol. 56:303-308, 1999), patients were seen by a behavioral neurologist who obtained a medical history from the patients and corroborating sources, and performed a variety of tests including the Short Test of Mental Status, Hachinski Ischemic Scale, and a neurologic examination. Other data collected included the Record of Independent Living, Geriatric Depression Scale, and additional family history information. as well as laboratory tests such as a chemistry group, complete blood cell count, vitamin B12 and folic acid levels, and thyroid-stimulating hormone levels. In this study, the first set of tests used for diagnostic purposes included the Wechsler Adult Intelligence Scale-Revised, Wechsler Memory Scale-Revised, Auditory verbal learning Test and Wide-Ragne Achievement test-III. A second set of tests, which were used for research purposes, included the Mini-Mental State Examination, dementia rating Scale, Free and Cued Selective Reminding test, Boston Naming Test, controlled Oral Word Association Test and category fluency procedures.

2. General Laboratory Procedures

When practicing the methods of the invention, a number of general laboratory tests can be used to assist in the progress of the DS patient being treated with GR antagonists, including monitoring of parameters such as blood cortisol, drug metabolism, etc. These procedures can be helpful because all patients metabolize and react to drugs uniquely. In addition, such monitoring may be important because each GR antagonist has different pharmacokinetics. Different patients and AP medications may require different dosage regimens and formulations. Such procedures and means to determine dosage regimens and formulations are well described in the scientific and patent literature. A few illustrative examples are set forth below.

a. Determining Blood Cortisol Levels

Varying levels of blood cortisol have been associated with DS, although the invention may also be practiced upon patients with apparently normal levels of blood cortisol. Thus, monitoring blood cortisol and determining baseline cortisol levels are useful laboratory tests to aid in preventing cognitive deterioration in DS patients. A wide variety of laboratory tests exist that can be used to determine whether an individual is normal, hypo- or hypercortisolemic. DS patients typically have normal levels of cortisol that are often less than 25 µg/dl in the morning, and frequently about 15 µg/dl or less in the afternoon, although the values often fall at the high end of the normal range, which is generally considered to be 5-15 µg/dl in the afternoon.

Immunoassays such as radioimmunoassays are commonly used because they are accurate, easy to do and relatively cheap. Because levels of circulating cortisol are an indicator of adrenocortical function, a variety of stimulation and suppression tests, such as ACTH Stimulation, ACTH Reserve, or dexamethasone suppression (see, e.g., Greenwald, Am. J. Psychiatry 143:442-446, 1986), can also provide diagnostic, prognostic or other information to be used adjunctively in the methods of the invention.

One such assay available in kit form is the radioimmunoassay available as "Double Antibody Cortisol Kit" (Diagnostic Products Corporation, Los Angeles, Calif.), (Acta Psychiatr. Scand. 70:239-247, 1984). This test is a competitive radioimmunoassay in which 125I-labeled cortisol competes with cortisol from an clinical sample for antibody sites. In this test, due to the specificity of the antibody and lack of any significant protein effect, serum and plasma samples require neither preextraction nor predilution. This assay is described in further detail in Example 2, below.

b. Determination of Blood/Urine Mifepristone Levels

Because a patient's metabolism, clearance rate, toxicity levels, etc. differs with variations in underlying primary or secondary disease conditions, drug history, age, general medical condition and the like, it may be necessary to measure blood and urine levels of GR antagonist. Means for such monitoring are well described in the scientific and patent literature. As in one embodiment of the invention mifepristone is administered to prevent cognitive deterioration in a DS patient, an illustrative example of determining blood and urine mifepristone levels is set forth in the Example below.

c. Other Laboratory Procedures

Because the mechanism of cognitive deterioration in DS patients may be complex, a number of additional laboratory tests can be used adjunctively in the methods of the invention to assist in diagnosis, treatment efficacy, prognosis, toxicity and the like. For example, diagnosis and treatment assessment can be augmented by monitoring and measuring glucocorticoid-sensitive variables, including but limited to fasting blood sugar, blood sugar after oral glucose administration, plasma concentrations thyroid stimulating hormone (TSH), corticosteroid-binding globulin, luteinizing hormone (LH), testosterone-estradiol-binding globulin, leptin, insulin, and/or total and free testosterone.

Laboratory tests monitoring and measuring GR antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to RU486) can be determined using, for example, thin layer chromatography, as described in Kawai *Pharmacol. and Experimental Therapeutics* 241:401-406, 1987.

3. Glucocorticoid Receptor Antagonists to Inhibit or Reverse Cognitive Deterioration in DS Patients The invention provides for methods of inhibiting or reversing cognitive deterioration in adults with DS utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below.

a. Steroidal Anti-Glucocorticoids as GR Antagonists.

Steroidal glucocorticoid antagonists are administered to inhibit or reverse cognitive deterioration in various embodiments of the invention. Steroidal antiglucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain (see, e.g., Lefebvre, J. Steroid Biochem. 33:557-563, 1989).

Examples of steroidal GR antagonists include androgen-type steroid compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, and 5,696,127. Such steroidal GR antagonists include cortexolone, dexamethasone-oxetanone, 19-nordeoxycorticosterone, 19-norprogesterone, cortisol-21-mesylate; dexamethasone-21-mesylate, 11β-(4-dimethylaminoethoxyphenyl)-17α-propynyl-17β-hydroxy-4,9-estradien-3-one (RU009), and 17β-hydroxy-17α-19-(4-methylphenyl) androsta-4,9(11)-dien-3-one (RU044).

i) Removal or Substitution of the 11-beta Hydroxy Group

Glucocorticoid agonists with modified steroidal backbones comprising removal or substitution of the 11-beta hydroxy group are administered in one embodiment of the invention. This class includes natural antiglucocorticoids, including cortexolone, progesterone and testosterone derivatives, and synthetic compositions, such as mifepristone (Lefebvre, et al. supra). Preferred embodiments of the invention include all 11-beta-aryl steroid backbone derivatives because these compounds are devoid of progesterone receptor (PR) binding activity (Agarwal, FEBS 217:221-226, 1987). Another preferred embodiment comprises an 11-beta phenyl-aminodimethyl steroid backbone derivative, i.e., mifepristone, which is both an effective anti-glucocorticoid and anti-progesterone agent. These compositions act as reversibly-binding steroid receptor antagonists. For example, when bound to a 11-beta phenyl-aminodimethyl steroid, the steroid receptor is maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-beta-hydrox-11-beta-(4-dimethylaminophenyl)17-alpha-(1-propynyl)estra-4,9-dien-3-one). Mifepristone has been shown to be a powerful antagonist of both the progesterone and glucocorticoid (GR) receptors. Another 11-beta phenyl-aminodimethyl steroids shown to have GR antagonist effects includes RU009 (RU39.009), 11-beta-(4-dimethyl-aminoethoxyphenyl)-17-alpha(propynyl-17-beta-hydroxy-4,9-estradien-3-one) (see Bocquel, J. Steroid Biochem. Molec. Biol. 45:205-215, 1993). Another GR antagonist related to RU486 is RU044 (RU43.044) 17-beta-hydrox-17-alpha-19-(4-methyl-phe-nyl)-androsta-4,9 (11)-dien-3-one) (Bocquel, 1993, supra). See also Teutsch, Steroids 38:651-665, 1981; U.S. Pat. Nos. 4,386,085 and 4,912,097.

One embodiment includes compositions containing the basic glucocorticoid steroid structure which are irreversible anti-glucocorticoids. Such compounds include alpha-keto-methanesulfonate derivatives of cortisol, including cortisol-21-mesylate (4-pregnene-11-beta, 17-alpha, 21-triol-3, 20-dione-21-methane-sulfonate and dexamethasone-21-mesylate (16-methyl-9 alpha-fluoro-1,4-pregnadiene-11 beta, 17 -alpha, 21-triol-3, 20-dione-21-methane-sulfonate). See Simons, J. Steroid Biochem. 24:25-32, 1986; Mercier, J. Steroid Biochem. 25:11-20, 1986; U.S. Pat. No. 4,296,206.

ii) Modification of the 17-beta Side Chain Group

Steroidal antiglucocorticoids which can be obtained by various structural modifications of the 17-beta side chain are also used in the methods of the invention. This class includes synthetic antiglucocorticoids such as dexamethasoneoxet-anone, various 17, 21-acetonide derivatives and 17-beta-carboxamide derivatives of dexamethasone (Lefebvre, 1989, supra; Rousseau, Nature 279:158-160, 1979).

iii) Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, Endocrinology 107:1278-1280, 1980).

In general, the 11-beta side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoid activity in comparison to 17-propinyl side chain containing compounds.

Additional glucocorticoid receptor antagonists known in the art and suitable for practice of the invention include 21-hydroxy-6,19-oxidoprogesterone (see Vicent, Mol. Pharm. 52:749-753, 1997), Org31710 (see Mizutani, J. Steroid Biochem Mol Biol 42(7):695-704, 1992), RU43044, RU40555 (see Kim, J. Steroid Biochem Mol Biol. 67(3):213-22, 1998), RU28362, and ZK98299.

b. Non-Steroidal Anti-Glucocorticoids as Antagonists

Non-steroidal glucocorticoid antagonists are also used in the methods of the invention to inhibit or reverse cognitive deterioration in DS individuals. These include synthetic mimetics and analogs of proteins, including partially peptidic, pseudopeptidic and non-peptidic molecular entities. For example, oligomeric peptidomimetics useful in the invention include (alpha-beta-unsaturated) peptidosulfonamides, N-substituted glycine derivatives, oligo carbamates, oligo urea peptidomimetics, hydrazinopeptides, oligosulfones and the like (see, e.g., Amour, Int. J Pept. Protein Res. 43:297-304, 1994; de Bont, Bioorganic & Medicinal Chem. 4:667-672, 1996). The creation and simultaneous screening of large libraries of synthetic molecules can be carried out using well-known techniques in combinatorial chemistry, for example, see van Breemen, Anal Chem 69:2159-2164, 1997; and Lam, Anticancer Drug Des 12:145-167, 1997. Design of peptidomimetics specific for GR can be designed using computer programs in conjunction with combinatorial chemistry (combinatorial library) screening approaches (Murray, J. of Computer-Aided Molec. Design 9:381-395, 1995; Bohm, J. of Computer-Aided Molec. Design 10:265-272, 1996). Such "rational drug design" can help develop peptide isomerics and conformers including cycloisomers, retro-inverso isomers, retro isomers and the like (as discussed in Chorev, TibTech 13:438-445, 1995).

Examples of non-steroidal GR antagonists include ketoconazole, clotrimazole; N-(triphenylmethyl)imidazole; N-([2-fluoro-9-phenyl]fluorenyl)imidazole; N-([2-pyridyl] diphenylmethyl)imidazole; N-(2-[4,4',4"-trichlorotrityl]oxyethyl)morpholine; 1-(2[4,4',4"-trichlorotrityl]oxyethyl)-4-(2-hydroxyethyl)piperazine dimaleate; N-([4,4',4"]-trichlorotrityl) imidazole; 9-(3-mercapto-1,2,4-triazolyl)-9-phenyl-2,7-difluorofluorenone; 1-(2-chlorotrityl)-3,5-dimethylpyrazole; 4-(morpholinomethyl)-A-(2-pyridyl) benzhydrol; 5-(5-methoxy-2-(N-methylcarbamoyl)-phenyl) dibenzosuberol; N-(2-chlorotrityl)-L-prolinol acetate; 1-(2-chlorotrityl)-2-methylimidazole; 1-(2-chlorotrityl)-1,2,4-triazole; 1,S-bis(4,4',4"-trichlorotrityl)-1,2,4-triazole-3-thiol; and N-((2,6-dichloro-3-methylphenyl)diphenyl) methylimidazole (see U.S. Pat. No. 6,051,573); the GR antagonist compounds disclosed in U.S. Pat. No. 5,696,127; the glucocorticoid receptor antagonists disclosed in Bradley et. al., J. Med. Chem. 45, 2417-2424 (2002), e.g., 4a(S)-Benzyl-2(R)-chloroethynyl-1,2,3,4,4a,9,10,10a(R)-octahydro-phenanthrene-2,7-diol ("CP 394531") and 4a(S)-Benzyl-2(R)-prop-1-ynyl-1,2,3,4,4a,9,10,10a(R)-octahydrophenanthrene-2,7-diol ("CP 409069"); the compound (11b, 17b)-11-(1,3-benzodioxol-5-yl)-17-hydroxy-17-(1-propynyl)estra-4,9-dien-3-one ("ORG 34517") disclosed in Hoyberg et al., Int'l J. of Neuro-psychopharmacology, 5:Supp. 1, S148 (2002); the compounds disclosed in PCT International Application No. WO 96/19458, which describes non-steroidal compounds which are high-affinity, highly selective antagonists for steroid receptors, such as 6-substituted-1,2-dihydro-N-protected-quinolines; and some κ opioid ligands, such as the κ opioid compounds dynorphin-1,13-diamide, U50,488 (trans-(1R,2R)-3,4-dichloro-N-methyl-N-[2-(1-pyrrolidinyl)cyclohexyl]benzeneacetamide), bremazocine and ethylketocyclazocine; and the non-specific opioid receptor ligand, naloxone, as disclosed in Evans et al., Endocrin., 141:2294-2300 (2000).

c. Identifying Specific Glucocorticoid Receptor Antagonists

Because any specific GR antagonist can be used to inhibit or reverse cognitive deterioration in adults with DS in the methods of the invention, in addition to the compounds and compositions described above, additional useful GR antagonists can be determined by the skilled artisan. A variety of such routine, well-known methods can be used and are described in the scientific and patent literature. They include in vitro and in vivo assays for the identification of additional GR antagonists. A few illustrative examples are described below.

One assay that can be used to identify a GR antagonist of the invention measures the effect of a putative GR antagonist on tyrosine amino-transferase activity in accordance with the method of Granner, Meth. Enzymol. 15:633, 1970. This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in cell extracts. TAT converts the amino group of tyrosine to 2-oxoglutaric acid. P-hydroxyphenylpyruvate is also formed. It can be converted to the more stable p-hydroxybenzaldehyde in an alkaline solution and quantitated by absorbance at 331 nm. The putative GR antagonist is co-administered with cortisol to whole liver, in vivo or ex vivo, or hepatoma cells or cell extracts. A compound is identified as a GR antagonist when its administration decreases the amount of induced TAT activity, as compared to control (i.e., only cortisol or GR agonist added) (see also Shirwany, Biochem. Biophys. Acta 886:162-168, 1986).

Further illustrative of the many assays which can be used to identify compositions utilized in the methods of the invention, in addition to the TAT assay, are assays based on glucocorticoid activities in vivo. For example, assays that assess the ability of a putative GR antagonist to inhibit uptake of 3H-thymidine into DNA in cells which are stimulated by glucocorticoids can be used. Alternatively, the putative GR antagonist can complete with 3H-dexamethasone for binding to a hepatoma tissue culture GR (see, e.g., Choi, et al., Steroids 57:313-318, 1992). As another example, the ability of a putative GR antagonist to block nuclear binding of 3H-dexamethasone-GR complex can be used (Alexandrova et al., J. Steroid Biochem. Mol. Biol. 41:723-725, 1992). To further identify putative GR antagonists, kinetic assays able to discriminate between glucocorticoid agonists and antagonists by means of receptor-binding kinetics can also be used (as described in Jones, Biochem J. 204:721-729, 1982).

In another illustrative example, the assay described by Daune, Molec. Pharm. 13:948-955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR antagonist) at varying concentrations. 3H-uridine is added to the cell culture, which is further incubated, and the extent of incorporation of radiolabel into polynucleotide is measured. Glucocorticoid agonists decrease the amount of 3H-uridine incorporated. Thus, a GR antagonist will oppose this effect.

For additional compounds that can be utilized in the methods of the invention and methods of identifying and making such compounds, see U.S. Pat. No. 4,296,206 (see above); U.S. Pat. No. 4,386,085 (see above); U.S. Pat. Nos. 4,447, 424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1,2-dihydro N-1 protected quinolines.

The specificity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606, 021; 5,696,127; 5,215,916; 5,071,773). Such an analysis can be performed using either direct binding assay or by assessing competitive binding to the purified GR or MR in the presence of a known antagonist. In an exemplary assay, cells that are stably expressing the glucocorticoid receptor or mineralocorticoid receptor (see, e.g., U.S. Pat. No. 5,606,021) at high levels are used as a source of purified receptor. The affinity of the antagonist for the receptor is then directly measured. Those antagonists that exhibit at least a 100-fold higher affinity, often 1000-fold, for the GR relative to the MR are then selected for use in the methods of the invention.

A GR-specific antagonist may also be defined as a compound that has the ability to inhibit GR-mediated activities, but not MR-mediated activities. One method of identifying such a GR-specific antagonist is to assess the ability of an antagonist to prevent activation of reporter constructs using transfection assays (see, e.g., Bocquel et al, J. Steroid Biochem Molec. Biol. 45:205-215, 1993; U.S. Pat. Nos. 5,606, 021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. A GR-specific antagonist is considered to exhibit at least a 100-fold, often 1000-fold or greater, activity towards the GR relative to the MR.

4. Inhibiting or Reversing Cognitive Deterioration Using Glucocorticoid Receptor Antagonists Antiglucocorticoids, such as mifepristone, are formulated as pharmaceuticals to be used in the methods of the invention to inhibit or reverse cognitive deterioration in DS patients. Any composition or compound that can block a biological response associated with the binding of cortisol or a cortisol analogue to a GR can be used as a pharmaceutical in the invention. Routine means to determine GR antagonist drug regimens and formulations to practice the methods of the invention are well described in the patent and scientific literature, and some illustrative examples are set forth below.

a. Glucocorticoid Receptor Antagonists as Pharmaceutical Compositions

The GR antagonists used in the methods of the invention can be administered by any means known in the art, e.g., parenterally, topically, orally, or by local administration, such as by aerosol or transdermally. The methods of the invention provide for prophylactic and/or therapeutic treatments. The GR antagonists as pharmaceutical formulations can be administered in a variety of unit dosage forms depending upon the condition or disease and the degree of psychosis, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's"). Therapeutically effective amounts of glucocorticoid blockers suitable for practice of the method of the invention will typically range from about 0.5 to about 25 milligrams per kilogram (mg/kg). A person of ordinary skill in the art will be able without undue experimentation, having regard to that skill and this disclosure, to determine a therapeutically effective amount of a particular glucocorticoid blocker compound for practice of this invention. For example, a particular glucocorticoid blocker may be more effective at higher or lower doses. By evaluating a patient using the methods described herein, a skilled practitioner will be able to determine whether a patient is responding to treatment and will know how to adjust the dosage levels accordingly.

In general, glucocorticoid blocker compounds may be administered as pharmaceutical compositions by any method known in the art for administering therapeutic drugs. Compositions may take the form of tablets, pills, capsules, semi-solids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Alfonso A R: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols.

Aqueous suspensions of the invention contain a GR antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GR antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Glucocorticoid blocker pharmaceutical formulations can be prepared according to any method known to the art for the manufacture of pharmaceuticals. Such drugs can contain sweetening agents, flavoring agents, coloring agents and preserving agents. Any glucocorticoid blocker formulation can be admixtured with nontoxic pharmaceutically acceptable excipients which are suitable for manufacture.

Typically, glucocorticoid blocker compounds suitable for use in the practice of this invention will be administered orally. The amount of a compound of this invention in the composition may vary widely depending on the type of composition, size of a unit dosage, kind of excipients, and other factors well known to those of ordinary skill in the art. In general, the final composition may comprise from 0.000001 percent by weight (% w) to 10% w of the glucocorticoid blocker compounds, preferably 0.00001% w to 1% w, with the remainder being the excipient or excipients. For example, the GR antagonist mifepristone is given orally in tablet form, with dosages in the range of between about 0.5 and 25 mg/kg, more preferably between about 0.75 mg/kg and 15 mg/kg, most preferably about 10 mg/kg.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Pharmaceutical preparations for oral use can be obtained through combination of glucocorticoid blocker compounds with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethyl-cellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

The GR antagonists of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The GR antagonists of this invention can also be administered by in intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

The GR antagonists of the invention can be delivered by transdermally, by a topical route, formulated as applicator sticks, solutions, suspensions, emulsions, gels, creams, ointments, pastes, jellies, paints, powders, and aerosols.

The GR antagonists of the invention can also be delivered as microspheres for slow release in the body. For example, microspheres can be administered via intradermal injection of drug (e.g., mifepristone)-containing microspheres, which slowly release subcutaneously (see Rao, *J. Biomater. Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The GR antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the GR antagonist formulations of the invention are useful for parenteral administration, such as intravenous (IV) administration. The formulations for administration will commonly comprise a solution of the GR antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR antagonist in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR antagonist formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR antagonist into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

b. Determining Dosing Regimens for Glucocorticoid Receptor Antagonists

The methods of this invention inhibit or reverse cognitive deterioration in adults with DS. The amount of GR antagonist adequate to accomplish this is defined as a "therapeutically effective dose". The dosage schedule and amounts effective for this use, i.e., the "dosing regimen," will depend upon a variety of factors, including the severity of cognitive deterioration, the patient's physical status, age and the like. In calculating the dosage regimen for a patient, the mode of administration also is taken into consideration.

The dosage regimen also takes into consideration pharmacokinetics parameters well known in the art, i.e., the GR antagonists' rate of absorption, bioavailability, metabolism, clearance, and the like (see, e.g., Hidalgo-Aragones, J. Steroid Biochem. Mol. Biol. 58:611-617, 1996; Groning, Pharmazie 51:337-341, 1996; Fotherby, Contraception 54:59-69, 1996; Johnson, J. Pharm. Sci. 84:1144-1146, 1995; Rohatagi, Pharmazie 50:610-613, 1995; Brophy, Eur. J. Clin. Pharmacol. 24:103-108, 1983; the latest Remington's, supra). For example, in one study, less than 0.5% of the daily dose of mifepristone was excreted in the urine; the drug bound extensively to circulating albumin (see Kawai, supra, 1989). The state of the art allows the clinician to determine the dosage regimen for each individual patient, GR antagonist and disease or condition treated. As an illustrative example, the guidelines provided below for mifepristone can be used as guidance to determine the dosage regiment, i.e., dose schedule and dosage levels, of any GR antagonist administered when practicing the methods of the invention.

Single or multiple administrations of GR antagonist formulations can be administered depending on the dosage and frequency as required and tolerated by the patient. The formulations should provide a sufficient quantity of active agent, i.e., mifepristone, to effectively inhibit or reverse cognitive deterioration in an adults with DS. For example, a typical preferred pharmaceutical formulation for oral administration of an antiglucocorticoid such as mifepristone or ORG 34517 would be about 5 to 15 mg/kg of body weight per patient per day, more preferably between about 8 to about 12 mg/kg of body weight per patient per day, most preferably 10 mg/kg of body weight per patient per day, although dosages of between about 0.5 to about 25 mg/kg of body weight per day may be used in the practice of the invention. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR antagonist formulations will be known or apparent to those skilled in the art and are described in more detail in such publications as Remington's, supra. See also Nieman, In "Receptor Mediated Antisteroid Action," Agarwal, et al., eds., De Gruyter, New York, 1987.

After a pharmaceutical comprising a GR antagonist of the invention has been formulated in a acceptable carrier, it can be placed in an appropriate container and labeled for treatment of an indicated condition. For administration of GR antagonists, such labeling would include, e.g., instructions concerning the amount, frequency and method of administration. In one embodiment, the invention provides for a kit for inhibiting or reversing cognitive deterioration in an adult with DS which includes a GR antagonist and instructional material teaching the indications, dosage and schedule of administration of the GR antagonist.

EXAMPLES

The following examples are offered to illustrate, but not to limit the claimed invention.

Example 1

Inhibiting or Reversing Cognitive Deterioration in Adult DS Patients with Mifepristone The following example demonstrates how to practice the methods of the invention.

Patient Selection:

Adults (over 18 years of age) who have been diagnosed with Down's Syndrome. The patient typically has normal levels of cortisol for his or her age.

Dosage Regimen and Administration of Mifepristone

The glucocorticoid receptor (GR) antagonist, mifepristone, is used in this study. It is administered in dosages of 200 mg daily. Individuals will be given 200 mg of mifepristone daily for six months and evaluated as described below. Dosages will be adjusted if necessary and further evaluations will be performed periodically throughout treatment.

Mifepristone tablets are available from commercial sources such as Shanghai HuaLian Pharmaceuticals Co., Ltd., Shanghai, China.

Assessing Cognitive Deterioration

To delineate and assess the effectiveness of mifepristone in inhibiting or reversing cognitive deterioration, the cognitive functioning of the patient is determined by objective and subjective criteria as described herein, and measured at baseline, 3 months, and 6 months.

Example 2

Measuring Cortisol Levels

To measure cortisol levels of the patients of Example 1, afternoon Cortisol Test measurements are taken and used as the baseline cortisol measure. Cortisol levels are taken at Day 0, at two weeks after receiving the medication (Day 14), and each visit for up to six months and periodically thereafter.

The "Double Antibody Cortisol Kit" (Diagnostic Products Corporation, Los Angeles, Calif.) is used to measure blood cortisol levels. This test is a competitive radioimmunoassay in which 125I-labeled cortisol competes with cortisol from an clinical sample for antibody sites, and is performed essentially according to manufacturer's instructions using reagents supplied by manufacturer. Briefly, blood is collected by venipuncture and serum separated from the cells. The samples are stored at 2 to 8° C. for up to seven days, or up to two month frozen at −20° C. Before the assay, samples are allowed to come up to room temperature (15-28° C.) by gentle swirling or inversion. Sixteen tubes in duplicate at 25 microliters of serum per tube are prepared. Cortisol concentrations are calculated from the prepared calibration tubes. Net counts equal the average CPM minus the average non-specific CPM. Cortisol concentrations for the unknowns are estimated by interpolation from the calibration curve (Dudley et al., Clin. Chem. 31: 1264-1271, 1985).

It is understood that the examples and embodiments described herein are for illustrative purposes only and that various modifications or changes in light thereof will be suggested to persons skilled in the art and are to be included within the spirit and purview of this application and scope of the claims.

What is claimed is:

1. A method of inhibiting cognitive deterioration in an adult patient with Down's syndrome but without dementia, the method comprising the step of administering to the patient an amount of a glucocorticoid receptor antagonist effective to inhibit cognitive deterioration, with the proviso that the patient be not otherwise in need of treatment with a glucocorticoid receptor antagonist.

2. The method of claim 1, wherein the glucocorticoid receptor antagonist comprises a steroidal skeleton with at least one phenyl-containing moiety in the 11-beta position of the steroidal skeleton.

3. The method of claim 2, wherein the phenyl-containing moiety in the 11-beta position of the steroidal skeleton is a dimethylaminophenyl moiety.

4. The method of claim 3, wherein the glucocorticoid receptor antagonist is mifepristone.

5. The method of claim 3, wherein the glucocorticoid receptor antagonist is selected from the group consisting of 11β-(4-dimethylaminoethoxyphenyl)-17α-propynyl-17β-hydroxy-4,9-estradien-3-one and 17β-hydroxy-17α-19-(4-methylphenyl)androsta-4,9(11)-dien-3-one.

6. The method of claim 1, wherein the glucocorticoid receptor antagonist is selected from the group consisting 4a(S)-Benzyl-2(R)-prop-1-ynyl-1,2,3,4,4a,9,10,10a(R)-octahydro-phenanthrene-2,7-diol and 4a(S)-Benzyl-2(R)-chloroethynyl-1,2,3,4,4a,9,10,10a(R)-octahydro-phenanthrene-2,7-diol.

7. The method of claim 1, wherein the glucocorticoid receptor antagonist is (11b, 17b)-11-(1,3-benzodioxol-5-yl)-17-hydroxy-17-(1-propynyl)estra-4,9-dien-3-one.

8. The method of claim 1, wherein the glucocorticoid receptor antagonist is administered in a daily amount of between about 0.5 to about 20 mg per kilogram of body weight per day.

9. The method of claim 8, wherein the glucocorticoid receptor antagonist is administered in a daily amount of between about 1 to about 10 mg per kilogram of body weight per day.

10. The method of claim 9, wherein the glucocorticoid receptor antagonist is administered in a daily amount of between about 1 to about 4 mg per kilogram of body weight per day.

11. The method of claim 1, wherein the administration is once per day.

12. The method of claim 1, wherein the mode of administration is oral.

13. The method of claim 1, wherein the patient is a young adult of between 21-35 years of age.

14. The method of claim 1, wherein the patient is a young adult of between 21-35 years of age and has no test evidence of cognitive deterioration.

15. The method of claim 1, wherein the mode of administration is by a transdermal application, by a nebulized suspension, or by an aerosol spray.

* * * * *